United States Patent [19]

Schurman et al.

[11] 4,358,859

[45] Nov. 16, 1982

[54] ARTICULATED PROSTHETIC KNEE AND METHOD FOR IMPLANTING SAME

[76] Inventors: David J. Schurman, 1044 Verier Pl.; Robert L. Piziali, 611 Salvatierra, both of Stanford, Calif. 94305

[21] Appl. No.: 81,713

[22] Filed: Oct. 4, 1979

[51] Int. Cl.³ .............................................. A61F 1/03
[52] U.S. Cl. ................................... 3/1.911; 128/92 C
[58] Field of Search ................ 128/92 C; 3/1.9, 1.91, 3/1.911

[56] References Cited

U.S. PATENT DOCUMENTS

| | | | |
|---|---|---|---|
| 3,696,446 | 10/1972 | Bousguet et al. | 3/1.911 |
| 3,813,700 | 6/1974 | Tavernetti et al. | 3/1.911 |
| 4,136,405 | 1/1979 | Pastrick et al. | 3/1.911 |

FOREIGN PATENT DOCUMENTS

| | | | |
|---|---|---|---|
| 2334265 | 1/1975 | Fed. Rep. of Germany | 3/1.911 |
| 1507309 | 4/1978 | United Kingdom | 3/1.911 |

*Primary Examiner*—Clifford D. Crowder

*Attorney, Agent, or Firm*—Townsend and Townsend

[57] ABSTRACT

An articulated knee prosthesis in which a femoral implant has a condyle section and a femoral stem that is cemented into the femur. A tibial implant carries a tibial plateau section on which is mounted a stop plate for engaging the condyle section and arresting movement of the knee beyond its fully extended position. The tibial implant includes a tibial stem that is cemented into the tibia. A pivotal connection between the two implants is positioned posteriorly of the implant and at an elevation above a lowermost point of the condyle section (when the implants are fully extended). The pivot axis of the connection and the stems are positioned with respect to each other so that upon the implantation of the implant, the patient's tibia is moved in an anterior direction as compared to the normal anatomical position of the tibia relative to the femur. At least a portion of the hinged connection, which frequently includes the pivot axis, is located posteriorly of portions of the femur proximate the knee joint to maximize the arc through which the knee can be flexed.

3 Claims, 3 Drawing Figures

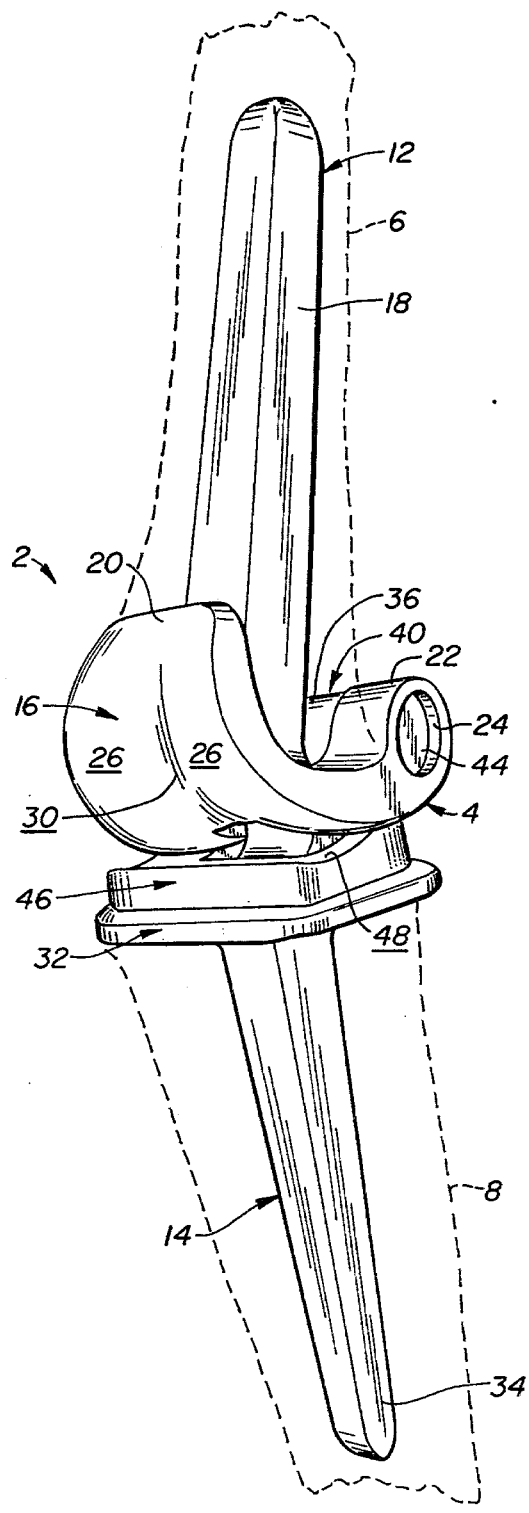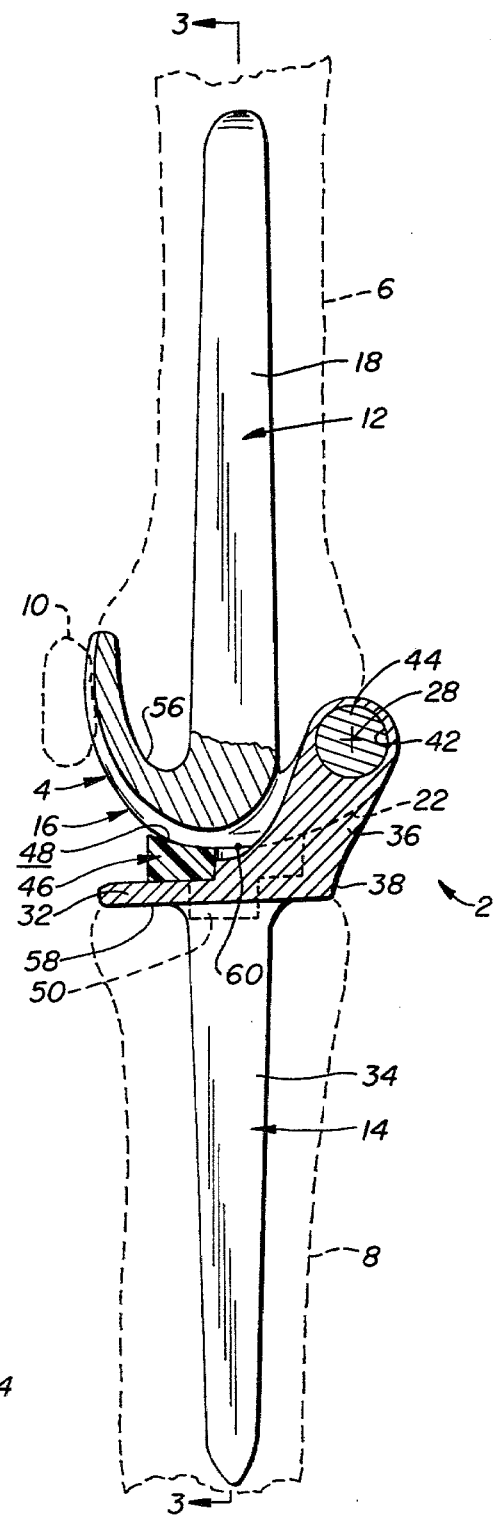
FIG._1. FIG._2.

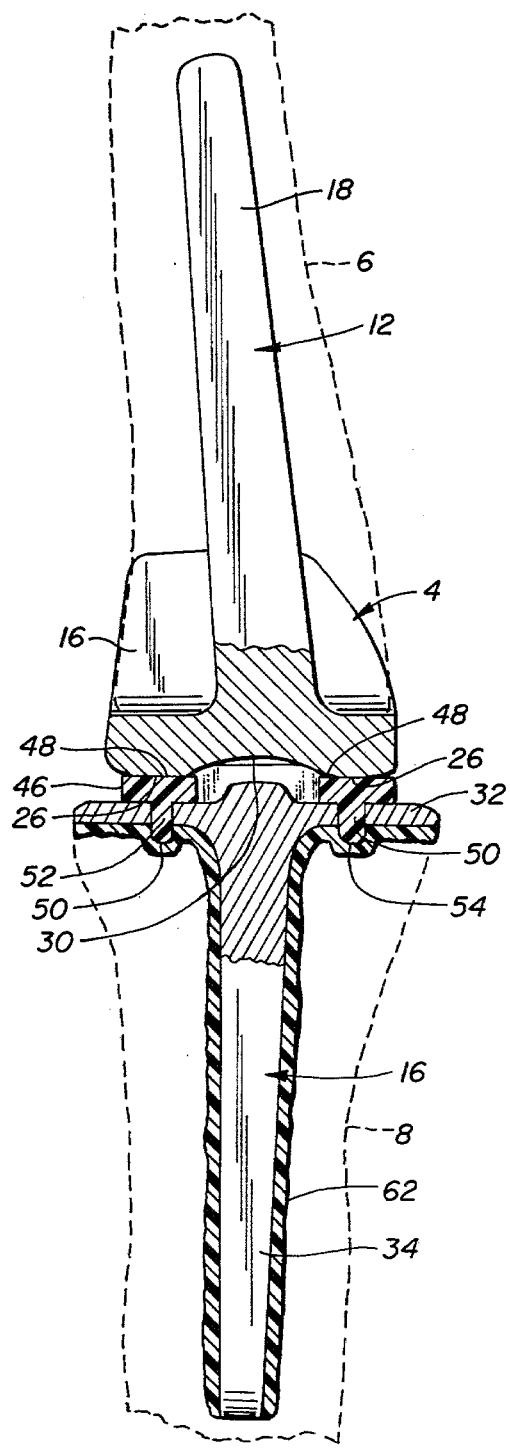
FIG._3.

ARTICULATED PROSTHETIC KNEE AND METHOD FOR IMPLANTING SAME

BACKGROUND OF THE INVENTION

This invention relates to an artificial knee prosthesis, or a prosthetic knee, for the replacement of a natural knee through surgical implantation.

In general, a natural knee is formed by the two condyles of the bottom part of the femur, the lower surfaces of which bear upon the complementarily shaped upper surface plateaus of the tibia through the intermediary of meniscii, a fibro-cartilage. Connection through the knee is provided by means of ligaments which also provide joint stability and help to absorb stresses applied to the knee. The femur, meniscii and tibia are normally subjected to relatively large forces in the course of supporting the major portion of a person's body weight.

Movement of the normal knee is complex, that is it is not simply a pivotal or rotational movement. Rather, a healty, natural knee has the ability to move in several distinct manners. Primarily, the natural knee joint permits flexion and extension between the femur and the tibia through an arc of about 135°. This motion is a combined rotational, rocking and gliding movement of successive points of the femoral condyles and the tibial plateaus. In addition, the healthy, natural knee permits a relative rotational movement between the condyles and the tibial plateaus as well as some limited relatively sliding motion (in conjunction with other knee motions) which might be described as taking place in a generally horizontal plane between the condyles and the plateau. The knee also permits a rolling-type motion, frequently referred to as abduction and adduction, between the condyles and the plateaus which might best be described as a limited rocking-type motion in a lateral direction, that is generally perpendicular to the plane in which the knee most commonly articulates (flexion and extension).

Aside from the proper geometric configuration of the condyles and the tibial plateaus, an effective, free movement of a natural knee in these directions requires the presence of a fibro-cartilage, commonly referred to as meniscus, between the condyles and the plateaus. When the meniscii becomes damaged, decreased on inflammed, they cease to function properly, the mobility of the knee joint becomes increasingly impaired and movements are accompanied by increasing severe pains.

To alleviate this condition, it is sometimes necessary to replace the natural knee by surgically implanting a prosthetic knee.

The prior art is replete with a great variety of prosthetic knees. In all instances, the prior art seeks to approximate the mobility of a natural knee to a greater or lesser extent by providing artificial substitutes for the condyle surfaces, the condyles as a whole, the entire lower portion of the femur, the tibial plateau or the entire upper portion of the tibia, including the plateau. The following U.S. Pat. Nos. disclose a variety of differently constructed and operating prosthetic knees:

No. 3,715,763
No. 3,774,244
No. 3,813,700
No. 3,824,630
No. 3,852,830
No. 3,924,277
No. 3,964,106
No. 4,000,525
No, 4,034,418

Further, the article "The Surgical Replacement of the Human Knee Joint" by D. A. Sonstegard, L. S. Matthews and H. Kaufer, published in the January 1978 issue (Vol. 238, No. 1) of Scientific American on pages 44–51, gives a good summary of the problems encountered with prosthetic knees and discusses the current state of the art in general terms.

There are two main types of prosthetic knees. The first type is an articulated device which provides a constraining mechanical linkage between the femoral and tibial implants; that is one in which the two implants are mechanically constrained to each other by means of a hinge, a ball and socket type joint, etc.

The second type of prosthetic knee is a non-constrained or unlinked device. In these devices, the emphasis is on replacing some or all of worn and/or deceased load bearing surfaces of the knee. They do not include a mechanical link, hinge, or similar constraint between the femoral and tibial implants. Instead, the stability of the prosthetic knee is primarily provided by the patient's ligaments and muscles.

The present invention relates to knees of the former type, namely constrained or articulated prosthetic knees.

Generally speaking, the replacement of an entire natural knee requires the surgical implantation of the prosthetic knee by removing at least portions of the femoral condyles and the tibial plateaus and implanting therein normally metallic substitutes referred herein as "femoral implants" and "tibial implants".

Although the exact construction of the femoral and tibial implants of such prosthetic knees and the exact manner in which they are connected to the femur and the tibia, respectively, varies, they all have the common characteristic that the implants are secured to the femur and the tibia with a bonding agent or cement.

The two implants of an articulated prosthetic knee are movably, normally pivotally interconnected so that they cannot move axially away from each other. Accordingly, such knees form a mechanical link between the patient's femur and tibia and they can be used when his ligaments are damaged or unusable.

The following is a list of relevant U.S. Pat. Nos. which disclose articulated knee prothesis:

3,760,427
3,795,922
3,824,630
3,837,009
3,848,276
3,909,854
3,918,101
3,934,272
3,969,773
4,001,896

Typically, these patents disclose prosthetic knees in which the relative motions between the femoral and the tibial implants are pivotal motions about a fixed pivot axis oriented transversely to the flexion-extension plane of the knee.

It is quite apparent that an articulated knee which incorporates a fixed pivot axis has a greatly reduced mobility or motion freedom as compared to a natural knee. In particular, such a knee is typically movable in only the primary direction, as above described, namely in the flexion-extension plane of the knee. Moreover, the pivotal articulation of the prosthesis is at best an approximation of the actual motion path of a natural knee, which as above-described, is a complex, arcuate and not a simple, circular path. The difference in the motion paths between a natural knee and a pivoted knee prosthesis causes the additional potential problems of (a) an interference of portions of the patient's femur and tibia which, if it is to be avoided, can severely limit the flexion-extension arc of the prosthesis as compared to that of a natural knee, (b) an adverse affect on the proper functioning of the muscles due to a change in the relative moment arms between the points on which the muscles act on the bones and the pivot axis, and (c) the generation of undesirable forces, bending moments and stresses in the cement interface between the implants and the corresponding bone structures.

It is quite apparent that these factors can adversely affect the operation of pivoted knee prosthesis. In addition, the expected service life might be shortened by them since, generally speaking, implanted knee prosthesis normally fail at the cement interface, and the generation of undesirable stresses often hastens such failures.

Thus, there is presently a need for an improved, pivotally articulated knee which provides a maximum, and ideally a full flexion-extension movement, which does not adversely affect the working of the associated muscles, and which protects the cement interface from stresses which can shorten the service life of the knee and/or result in its premature failure.

SUMMARY OF THE INVENTION

The present invention is directed to a pivotally articulated knee which overcomes the shortcomings encountered with such prior art knees by positioning the pivot axis relatively posteriorly and at a somewhat raised elevation as is described in greater detail below so that the knee can move through substantially the full flexion-extension arc of about 135°. Further, the knee is constructed so that upon its implantation in the femur and the tibia the position of the latter with respect to the former is altered from the normal, anatomical position (i.e. the position of the tibia when the knee is a natural, healthy knee) by moving the tibia in an anterior direction. As a result, the motion freedom of the articulated knee is substantially equal to the motion freedom of a natural knee since the positioning of the pivot axis is such that tissue (e.g. bone) interference as the knee approaches its fully flexed position is eliminated.

Further, the knee of the present invention can be implanted in and aligned with the patient's femoral and tibial (bone) canals without requiring a relative offset, angular inclination or the like of the implant in general and of the implantation stems in particular. Consequently, adverse forces, bending moments and stresses in the cement interface and a resulting shortened service life are eliminated. Moreover, as will be further described below, the knee is constructed so as to effectively increase the lever arm for the patient's quadricep muscles and thereby effectively strengthens the patient's leg without correspondingly weakening other muscles.

Thus, an articulated knee prosthesis constructed in accordance with the present invention gives a patient greater enhanced mobility as compared with prior art, pivotally articulated knee implants, better strength and an enhanced service life.

Generally speaking, the present invention accomplishes this by providing a pivotally articulated knee prosthesis comprising a femoral implant including a condyle section and an elongated femoral stem protruding from the section for implantation in the femoral canal of the patient. A tibial implant includes a tibial plateau section and an elongated tibial stem which protrudes from the plateau section and which is implanted in the tibial canal of the patient. A pivotal connection between the implants is positioned proximate posterior portions thereof and permits relative pivotal motion of the implants about a pivot axis between an extended position in which the stems are in substantial alignment and a flexed position in which the stems are obliquely inclined relative to each other. The pivot axis is oriented transversely to the stems and is positioned relative to the stems so that the implantation of the stems in the respective bone canals causes a shift in the position of the patient's tibia relative to his femur in an anterior direction as compared with the anatomically normal position of the tibia relative to the femur.

This is accomplished by providing first and second hinge flanges which protrude from the condyle section and the tibial plateau section, respectively, in a generally posterior and upward (in regard to a person's anatomical, i.e. standing position) direction so that the pivot axis is relatively proximiate the patient's femur and remote from his tibia.

Preferably, at least a portion of the flanges and frequently a portion of the pivot pin, including the pivot axis are positioned posterior of the femur and the tibia. The resulting position of the pivot axis approximates the more complex motion path of a natural knee in what applicant's consider the best possible manner. Simultaneously, it prevents an interference at the flexed knee position of the femur and the tibia while it permits the implantation of the stems in the respective bone canals without any relative offset or angular inclination between the implantation stems and the canals. This not only facilitates the implantation procedure but prevents such offsets of the stems relative to the canal walls from generating bending moments and associated, undesirable stresses.

In a more specific, preferred embodiment, the condyle section defines a pair of spaced apart condyle surfaces which are interconnected by a depression shaped for engaging the patella of the patient and preventing lateral excursions of the patella when the knee is moved between its extended and flexed positions.

The knee prosthesis of the present invention further includes a plate member constructed of a slightly resilient material such as high molecular weight polyethylene or the like which is secured to the tibial plateau section. The latter is shaped as a generally flat platform and includes apertures through which posts integrally constructed with the plate member extend. The posts are longer than the thickness of the platform so that they protrude from an underside thereof and become embedded in the cement interface. This securely attaches the plate member to the tibial implant and structurally integrates it with the tibia, the cement interface and the tibial implant, thereby eliminating all possibility of relative motions which, if they are allowed to exist over prolonged of time might lead to a loosening of the cement interface and a resulting failure of the implant.

The resilient plate member has an upper surface which is shaped to engage the condyle surface of the condyle section when the implants are in their fully extended position. At that point, any further forces applied by the patient's muscle structure to move the implants beyond the fully extended position result in the application of compressive forces to the plate member which resists such further movement in a slightly yielding manner, thereby preventing abrupt stops in the pivotal movement of the implant into the extended position which, if permitted to resist, can cause damage to the bone structure and/or the cement interface. The resilient plate member experiences only compressive forces and is not subjected to relative sliding engagement by the condyle section of the femoral implant. Thus, the resilient plate member experiences substantially no wear which enhances the maintenance-free service life of the prosthesis.

In addition, the present invention provides a method for implanting a pivotally articulated knee as above-described which includes the steps of providing a femoral impant including a condyle section and an elongated femoral stem protruding therefrom; a tibial implant including a tibial plateau section and an elongated tibial stem protruding therefrom; implanting the femoral implant in the patient's femur by positioning the femoral stem in the patient's femoral canal and in substantial alignment therewith; and implanting the tibial stem in the patient's tibial canal and in substantial alignment therewith. The implants are pivotally interconnected for relative pivotal motion between them between an extended position in which the tibia and the femur are in substantial alignment and a flexed position in which they are obliquely inclined. The method further includes the step of positioning the pivoted axis about which the implants move so that the patient's tibia is positioned anterior of its normal, anatomical position to provide the above discussed advantages.

In conformity with the construction of the prosthesis itself, the method of the present invention further includes the steps of providing first and second flanges attached to the femoral implant and the tibial implant, respectively, which have holes that are concentric with the pivot axis, and placing a hinge pin in the holes to thereby hingedly interconnect the flanges, and further the step of positioning at least a portion of the flanges posteriorly of the patient's femur and tibia.

From the foregoing, it should be apparent that the present invention provides a substantial improvement in the construction and operation of as well as in the implantation procedure for pivotally articulated prosthetic knees.

BRIEF DESCRIPTION OF THE DRAWINGS

FIG. 1 is a perspective, elevational view of an articulated prosthetic knee constructed in accordance with the present invention and illustrates the prosthetic knee in a partially flexed position;

FIG. 2 is a side elevational view, partially in section, of the prosthetic knee illustrated in FIG. 1 and FIG. 3 is a rear elevational view, partially in section, and is taken on line 3—3 of FIG. 2.

DESCRIPTION OF THE PREFERRED EMBODIMENTS

Referring to the drawings, a human knee joint 2 is formed by an articulated knee prosthesis 4 which is implanted into the femur 6 and the tibia 8 of a human in the manner more fully discussed below. As is well known, the lower end of the femur terminates in natural condyles (not shown) which are received by dished-in meniscii (not shown) carried on an upper end of the tibia. A natural human knee also includes a patella 10 located anteriorly of the knee.

Three basic groups of muscles, not shown in the drawings, provide the forces required for the functioning of the knee. The hamstring group and the gastrocnemius group contract to make the leg bend or flex at the knee. The quadriceps group, utilizing the mechanical advantage provided by the patella, straightens or extends the leg.

The ligaments of the knee (not shown in the drawing) are pliant and flexible so that they allow a considerable but nonetheless remarkably controlled freedom of movement. Along their length, the ligaments form strong and relatively inextensible connections of bone to bone, thereby providing both stability to the joint and constraint of motion. The patellar ligament links the patella and the tibia and provides a sliding motion at the patella-femoral articulation during flexion and extension, and transmit forces generated by the quadriceps group of muscles across the knee joint.

To facilitate the understanding of the invention, the following, frequently used terms have the following meaning unless otherwise indicated. "Up" and "down" refer to a relatively raised or lowered elevation when a human is in the anatomical position, i.e. when he is standing upright and faces forward. The terms "anterior" and "posterior" mean forward and rearward, respectively, with respect to a side view of the knee. Thus, the patella 10 illustrated in FIG. 2 is anterior of the main knee joint while the pivot axis (further defined below) is posterior of the main knee joint. The knee is considered in its "extended" position when the femur 6 and tibia 8 are in substantial alignment (as viewed in side elevation) as is illustrated in FIG. 2. In a "flexed" position the femur and the tibia are obliquely inclined with respect to each other as is illustrated, for example, in FIG. 1. strong and relatively inextensible connections of bone to The term "canal" refers to the bone canals found at the centers of the femur and the tibia, respectively, which in more exacting language are frequently defined as intramedullary spaces in these long bones. Lastly, "normal anatomical position" refers to the relative position of one body part with respect to another without outside interference, e.g. the "normal anatomical position" of the tibia is the position taken by the tibia relative to the femur when the human has a healthy, natural knee.

Referring again specifically to the drawings, the articulated prosthesis of the present invention generally comprises an upper, femoral implant 12 which is hingedly connected to a lower tibial implant 14. The implants are cemented to the femur 6 and the tibia 8, respectively, as is more fully described below.

The femoral implant 12 includes a condyle section 16 which is a flange plate having a generally arcuate shape and an elongated, femoral stem 18 which, when the prosthesis is in its extended position, extends upwardly from the condyle section. The stem and the condyle section are integrally constructed of a material capable of withstanding the body environment such as stainless steel, an alloy of cobalt, chromium and molybedum, titanium, or a similar suitable material.

The condyle section has a generally arcuate configuration and extends over an arc of at least about 90° and more typically over an arc of between 120° to 140°. Its posterior end is defined by a pair of spaced apart, posteriorly and upwardly facing flanges 22 which include aligned bores 24. The free or anterior end 20 of the condyle section is generally upwardly oriented.

The condyle section defines a pair of spaced apart, downwardly and anteriorly facing condyle surfaces 26. The condyle surfaces are compoundly curved, i.e. in their longitudinal direction, they (together with the entire flange plate of the condyle section) are convexly curved about a pivot axis 28 defined by bores 24. They are also convexly curved in a lateral direction, generally perpendicular to the curvature of the flange plate of the condyle section. A transversely concavely curved, outwardly or anteriorly open depression, also defined by the condyle section, joins and provides continuity between the two condyle surfaces 26. The concave curvature of the depression is generally perpendicular to pivot axis 28.

The depression 30 between the two condyle surfaces 26 is formed to receive the patient's natural patella 10 (or an artificial patella button) and it is given a sufficient depth so that lateral excursions of the patella during flexion and extension of the knee joint are prevented. In a practical embodiment, the depression is about 4 to 8 mm deep and typically it is in the range of between 5 to 6 mm deep. It extends over the full length of the condyle surfaces from adjacent free end 20 of the condyle section to the open space 40 between flanges 22 so that a lateral movement restraint is formed for the patella irrespective of whether the knee is fully extended, fully flexed or at an intermediate position.

The tibial implant 14 defines a tibial plateau in the form of a generally flat, typically rectangularly shaped platform 32 from which an elongated, tibial stem 34 projects in a downward direction. The platform and the stem are again integrally constructed of a suitable metal.

A flange 36 extends posteriorly and upwardly from a posterior boundary 38 of the platform, is located so that it extends into a space 40 between flanges 22 on femoral implant 12, and terminates in a bore 42 which is aligned with bores 24 in the flanges 22 of the femoral implant. A pivot pin 44 extends through bores 24, 42 and pivotally secures the two implants to each other.

For purposes more fully discussed below, a stop plate 46 is secured to the upwardly facing side of platform 32. The stop plate is preferably constructed of a slightly resilient material, i.e. a material which has greater resiliency than metal such as steel when subjected to compression but less resiliency than materials such as most rubbers. High molecular weight polyethylene is a presently preferred material of this type. The stop plate has an upwardly facing, concave surface 48 shaped complementary to the downwardly facing condyle surfaces 26 and the plate is positioned so that the concave surface engages the femoral implant when the implants are in the fully extended position illustrated in FIG. 2.

The stop plate includes a pair of downwardly facing posts 50 which straddle the tibial stem 34 and which extend through suitably shaped apertures 52 in the platform. The length of the stems exceeds the thickness of the platform so that lower ends 54 of the posts thereof protrude downwardly from the downwardly facing side of the platform.

From the foregoing description, it will be apparent that the prosthetic knee 4 of the present invention can pivot between an extended position (shown in FIG. 2) and a flexed position until there is some interference between parts of the knee. In practice, the knee can be flexed through an arc somewhat in excess of 180° at which point intermediate portions of the femoral and tibial stems 18, 34, touch. Attempts to move the implants from the flexed position beyond the fully extended position are not possible because once the implants arrive at the fully extended position, the application of a force to move the implants beyond that position is opposed by stop plate 46. Such a force stresses the stop plate in compression and, to the extent the stop plate exhibits resiliency, prevents abrupt, shocklike stops. However, movements beyond the fully extended position are not possible.

Further, the stop plate has a plan configuration which approximates that of the tibial implant platform 32, but it is of a slightly lesser size so as to not protrude beyond the boundaries of the platform.

The implants 12, 14 are implanted by appropriately sculpturing the lower end of the femur and the upper end of the tibia so that the upwardly facing surface 56 of the condyle section 16 and the downwardly facing surface 58 of the platform 32 rest accurately against the bones. A center hole is formed through the lower and upper ends of the femur and the tibia, respectively, into the respective bone canals (not separately shown in the drawings) and thereafter, the stems 18, 34 of the implants are axially inserted into the canals, permitting the stems to center themselves in the canals. A suitable cement, such as polymethyl methacrylate is placed between the opposing surfaces of the bones and the implants and upon hardening the cement forms an interface 62 between the two and attaches the implants to the respective bones. During implantation, the implants are carefully aligned and after the cement has been applied, they are interconnected by inserting pivot pin 44 into the aligned flange bores 24 and 42. The pivoting, articulated prosthetic knee of the present invention is thereby in place and allows relative pivotal motion in the flexion-extension plane of the knee, that is in a plane perpendicular to pivot axis 28.

The extended knee position is determined by the interengagement between the condyle surfaces 26 and the upwardly facing surfaces 48 of the stop plate 46. No such stop, however, is available or desirable to determine the fully flexed position. Instead, upon flexure of the articulated knee, a mass of soft tissue tends to accumulate posteriorly of the knee and limits flexion in a gradual manner so long as an interference between bone structures is prevented. In order to prevent such bone interference, which is not only painful, but which can injure tissue and/or can cause the generation of excessive forces in the cement interface between the implants and the respective bones, the flanges are formed so that the pivot axis 28 is (a) relatively closer to the patient's femur than to his tibia, that is so that the pivot axis is above a lowermost point 60 of the condyle surfaces (when the knee is extended) and (b) so that the pivot axis is generally posteriorly of the knee joint.

In regard to the latter, the flanges are formed so that at least a portion thereof is posterior of the femur and the tibia when the knee is in its extended position. Normally the flanges are formed so that at least a portion of the pivot shaft 44 and for instances in which the pivot shaft diameter is in the range of up to about 12 mm frequently also the pivot axis 28 is posterior of the (posteriormost) surface of the femur and the tibia in the immediate vicinity of the knee joint. In a presently preferred embodiment, the pivot axis is further between about 10 to 20 mm and preferably approximately 15 mm above the lowermost point 60 of the condyle surfaces 26 when the knee is extended.

When so constructed, the articulated knee of the present invention, though not a perfect substitute for a natural knee, nevertheless allows flexion of the prosthetic knee through an arc of as much as 120° to 125° without bone contact or interference and the termination of the flexion results from a general accumulation of soft tissue on the posterior side of the knee joint in a desirably gradual manner.

It is applicants' observation that the above described position of the pivot axis 28 comes as close to duplicating the motion path of a natural knee as is possible with the inherent restraints of a pivoted knee joint, keeping in mind that the natural knee motions are not pivotal but compoundly curved motions.

In addition to the positioning of the pivot axis the present invention locates the femoral and tibial stems 18, 34 so that upon the implantation of the stems in the respective bones, the patient's tibia 8 is moved in an anterior direction as compared with its natural anatomic position by between about 6 mm to about 7 mm and preferably in the vicinity of about 6.8 mm. This not only aids in avoiding bone interference when the knee is fully flexed, but further makes it possible to insert the tibial stem 34 substantially concentrically into the tibial bone canal; in other words, the stem need not be eccentrically positioned in the bone canal (which is most difficult to achieve) or tilted (which would cause the formation of undesirable forces and stresses from bending moments and the like) which severely stress the cement interface and may lead to its premature failure.

In this connection, an additional advantage obtained from placing the pivot axis 28 at a point substantially more posterior than was heretofore the case can be observed. The quadricep muscle group is connected via ligaments with the patella as above briefly outlined and, when they apply a force they bias the patella firmly into the depression 30. In addition, the extending force exerted by the quadricep muscle group operates with the help of a moment arm between the patella and the pivot point of the knee joint. In a natural knee that pivot point varies constantly but is generally in the vicinity of the center of the knee. In the prosthetic knee of the present invention, that pivot point is substantially more posterior than in a natural knee which substantially increases the lever arm with which the quadricep muscle group extends the knee and thereby increases the power that can be exerted with it.

We claim:

1. An articulated knee prosthesis comprising a femoral implant including a condyle section and an elongated femoral stem protruding from the section for implantation in the femoral canal of a patient; a tibial implant including a tibial plateau section and an elongated tibial stem protruding from the plateau section for implantation in the tibial canal of a patient; the implants defining an anterior implant portion and a posterior implant portion; hinge means interconnecting the implants, positioned proximate the posterior portions of the implants and permitting relative pivotal motion of the implants about a pivot axis defined by the hinge means between an extended position in which the stems are in substantial alignment and a flexed position in which the stems are obliquely inclined relative to each other; the pivot axis being oriented transversely to the stems and positioned relative to the stems so that the implantation of the stems in the respective canals causes a shift in the position of the patient's tibia relative to the femur in an anterior direction as compared with the anatomically normal position of the tibia with respect to the femur; means constructed of a resilient material, disposed between the implants and shaped and positioned to engage the sections of the implants when the implants are in their extended position and to prevent movement of the implants beyond the extended position; the resilient means comprising a plate member having upper and lower surfaces shaped to correspond to opposing surfaces defined by the implant sections for engaging such surfaces and thereby limiting relative movement between the implants beyond the extended position; the tibial plateau section defining a generally flat platform, and including means for securing the plate member to the platform; and the securing means comprising at least one post protruding from the plate member towards the platform and having a length greater than a corresponding thickness of the platform, and an aperture formed in the platform sized and positioned to receive the post so that a free end of the post protrudes from an underside of the platform facing the patient's tibia; whereby upon the implantation of the tibial implant and its attachment to the patient's tibia with cement, the cement also bonds to the post and thereby structurally integrates the post with the platform, the cement and the patient's tibia.

2. A method for implanting an articulated knee as a replacement of the natural knee of a patient comprising the steps of providing a femoral implant including a condyle section and an elongated femoral stem protruding from the section; providing a tibial implant including a tibial plateau section and an elongated tibial stem protruding from the plateau section; implanting the femoral implant in the patient's femur by positioning the femoral stem in the patient's femoral canal and in substantial alignment therewith; implanting the tibial implant in the patient's tibia by positioning the tibial stem in the patient's tibial canal and in substantial alignment therewith and cementing the respective implants to the femur and the tibia by applying a bonding agent therebetween; providing a resilient plate member; positioning the plate member between opposing surfaces of the sections so that the plate member is compressed when a force is applied to the implant which tends to move the implants beyond their fully extended position; embedding a portion of the plate member in the bonding agent so that the plate member is directly secured to and structurally integrated with the patient's tibia; pivotally interconnecting the implants about a pivot axis for pivotal motion of the implants and therewith of the patient's tibia relative to the patient's femur between an extended position in which the tibia and the femur are in substantial alignment and a flexed position in which they are obliquely inclined; and positioning the pivot axis about which the implants pivot so that the patient's tibia is positioned anterior of its normal, anatomical position.

3. An articulated knee prosthesis comprising a femoral implant including a condyle section and an elongated femoral stem protruding from the section for implantation in the femoral canal of a patient; a tibial implant including a tibial plateau section and an elongated tibial stem protruding from the plateau section for implantation in the tibial canal of a patient; the implants defining an anterior implant portion and a posterior implant portion; a plate member having upper and lower surfaces shaped to correspond to opposing surfaces defined by the implant sections for engaging such surfaces and thereby limiting relative movement between the implants beyond the extended position; said plate member includes a post extending therefrom and through an aperture in said plateau section so that a free end of the post protrudes from an underside of the plateau section facing the patient's tibia; whereby upon the implantation of the tibial implant and its attachment to the patient's tibia with cement, the cement also bonds to the post and thereby structurally integrates the post with the plateau section, the cement and the patient's tibia; hinge means interconnecting the implants, positioned proximate the posterior portions of the implants and permitting relative pivotal motion of the implants about a pivot axis defined by the hinge means between an extended position in which the stems are in substantial alignment and a flexed position in which the stems are obliquely inclined relative to each other.

* * * * *